United States Patent [19]

Lewis

[11] Patent Number: 4,489,216

[45] Date of Patent: Dec. 18, 1984

[54] HYDROCARBON ISOMERIZATION

[75] Inventor: Paul H. Lewis, Groves, Tex.

[73] Assignee: Texaco Inc., White Plains, N.Y.

[21] Appl. No.: 342,546

[22] Filed: Jan. 25, 1982

[51] Int. Cl.$^3$ .............................................. C07C 5/24
[52] U.S. Cl. .................................. 585/739; 585/481;
    585/670; 585/671; 502/64; 502/78
[58] Field of Search ............... 585/481, 739, 475, 734,
    585/482, 666, 670, 671; 502/78

[56] References Cited

U.S. PATENT DOCUMENTS

| | | | |
|---|---|---|---|
| 3,281,482 | 10/1966 | Dvoretzky et al. | 585/481 |
| 3,442,794 | 5/1969 | Van Helden et al. | 585/739 |
| 3,507,931 | 4/1970 | Morris et al. | 585/739 |
| 3,792,098 | 2/1974 | Brandenburg et al. | 585/481 |
| 3,812,199 | 5/1974 | Chen et al. | 585/739 |
| 4,232,181 | 11/1980 | Kiovsky et al. | 585/739 |

FOREIGN PATENT DOCUMENTS 4046606 12/1970 Japan .................................. 585/481

Primary Examiner—Delbert E. Gantz
Assistant Examiner—A. Pal
Attorney, Agent, or Firm—Robert A. Kulason; Carl G. Seuttor

[57] ABSTRACT

Isomerization is effected at improved conversion and selectivity by use of a 0.5 w %–2.5 w % platinum-palladium group metal on hydrogen mordenite catalyst, silica to alumina mole ratio in the range of 10:1 to 20:1, the catalyst having been calcined at 1200° F.–1500° F. prior to use whereby it acquires activated sites not present in mordenite calcined at lower temperature.

5 Claims, No Drawings

HYDROCARBON ISOMERIZATION

FIELD OF THE INVENTION

This invention relates to hydrocarbon conversion. More specifically it relates to the isomerization of hydrocarbons.

BACKGROUND OF THE INVENTION

As is well known to those skilled in the art, hydrocarbons may be isomerized to form more desired products in the presence of various catalysts typified by mordenite catalysts. Illustrative of prior art showing mordenite catalysts and its use in hydrocarbon processing may be noted U.S. Pat. No 3,507,931
U.S. Pat. No. 3,190,939
U.S. Pat. No. 3,539,498
U.S. Pat. No. 3,831,597
U.S. Pat. No. 3,925,503
Brit. No. 1,088,933 etc.

In isomerization processes, a principal problem is the attainment of high yield and selectivity of desired isomates; and minimization of competing reactions is a desiderata. A principal undesired competing reaction is cracking; and a common measure of effectivity of an isomerization catalyst is its ability to maximize isomerization while minimizing cracking.

It is an object of this invention to provide a process for isomerization. Other objects will be apparent to those skilled in the art.

STATEMENT OF THE INVENTION

In accordance with certain of its aspects, this invention is directed to a method of preparing a catalyst which comprises loading a hydrogen mordenite, having a silica-to-alumina mole ratio of 10–50.1, with a metal of the platinum-palladium group thereby forming a loaded hydrogen mordenite; calcining said loaded hydrogen mordenite at 1200° F.–1500° F. thereby forming a calcined hydrogen mordenite containing activated isomerization sites; and recovering said calcined hydrogen mordenite containing activated isomerization sites.

DESCRIPTION OF THE INVENTION

The charge composition which may be used in practice of the invention is a particular form of crystalline alumino-silicate known as mordenite. Although mordenite is naturally occurring in the sodium form, synthetic mordenites have become commercially available and are extremely useful in the process of our invention. In its sodium form, mordenite usually has minimal catalytic activity and must therefore be converted to the hydrogen or decationized form before it finds utility in catalytic processes.

Mordenite structures are characterized by parallel sorption channels of uniform cross-section. The sorption channels are parallel to the C-axis of the crystal and are elliptical in cross-section. The sorption channels of sodium mordenite, based on crystallographic studies, have been reported as having a minor diameter of 6.7 A., a major diameter of 7.0 A., and a free diameter of 6.6 A., the hydrogen form of mordenite is believed to have a slightly larger free diameter.

Although mordenite occurs in nature, synthetic mordenites are commercially available from the Norton Company under the trade name Zeolon. Thes mordenites have a chemical composition on a unit cell basis, of

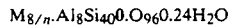

$$M_{8/n}\cdot Al_8Si_{40}O_{96}0.24H_2O$$

where M may be sodium, hydrogen or some other exchangeable cation and n is the valence of the cation. The high ratio of silica to alumina of 10:1 in the synthetic mordenite permits complete acid exchange to a stable hydrogen form and imparts excellent chemical and thermal stability. The effective working diameter of the channels in hydrogen mordenite (prepared by acid treating synthetic sodium mordenite), marketed under the trade name Zeolon H, appears to be in the range of 7.6 to 8.5 A. as indicated by adsorption of aromatic hydrocarbons.

Structurally mordenite is significantly distinguishable from other zeolites. Mordenite's tube-like gas sorption chambers have but two openings thru which hydrocarbon molecules can pass. In contrast the sorption chamber in Type A zeolite has six windows or pore openings through which hydrocarbons can pass. The sorption chambers in X and Y zeolites have four windows.

The sodium form of mordenite is not effective for isomerization regardless of whether the temperature is within the range unusually employed to effect paraffin isomerization and regardless of catalyst additions. However, the hydrogen form of synthetic mordenite having a sodium content of less than 5 weight percent is exceptionally effective for converting paraffins to their isomers. Decationized mordenite, i.e. mordenite in the hydrogen form, may be produced by the exchange of the sodium in the mordenite with ammonium ions followed by heating or calcining to drive off ammonia.

An extremely effective method of producing the decationized mordenite is by acid treatment of mordenite charge which has been calcined at typically 1200° F.–1500° F., say 1292° F. for 1–12 hours preferably 2 hours. In addition to decationizing the calcined mordenite, acid treatment may also remove some of the aluminum from the zeolitic structure, thereby increasing the relative proportion of silica to alumina in the zeolite. In its sodium form, both natural and synthetic mordenite have a mole ratio of silica to alumina of about 10 to 1. Hydrogen mordenite also has a silica to alumina mole ratio of about 10 to 1, but treating the sodium mordenite with dilute acid to produce the decationized form may remove aluminium sufficiently to increase the silica to alumina ratio slightly above 10 to 1.

The acid leaching used to produce the mordenite catalysts employed in the process of this invention must be severe enough to substantially increase the silica to alumina mole ratio of the mordenite to above about 10:1. However, the acid leaching must not be so severe as to destroy the crystalline structure of the mordenite. Further, little improvement has been observed in our isomerization process where the silica to alumina ratio of the mordenite is greater than about 50:1.

Consequently, as a practical limit the acid leaching should be severe enough to produce a mordenite having a silica to alumina ratio between 10:1 and 50:1, preferably between about 10:1 and 30:1.

Acid leaching of calcined mordenite may be suitably effected with mineral acids which will selectively remove aluminum without destroying the zeolitic crystalline structure, for example, hydrochloric or sulfuric acid. Boiling dilute hydrochloric acid is extremely effective in removing the aluminum.

Although we have described an acid leaching technique for preparing the mordenite catalysts used in our process, hydrogen mordenites having silica to alumina mole ratio between about 10:1 and about 50:1 prepared by other methods may also be employed in our process.

The hydrogen mordenite catalyst support so prepared is preferably water-washed and calcined in air at 1000° F.–1500° F., say 1300° F., for typically 15 hours.

Whether or not the hydrogen mordenite is prepared by exchange of $NH_4^+$ for $Na+$ or by leaching with acid such as hydrochloric acid, prior art teaching indicates that the acid mordenite should not be calcined to temperature above about 1000° F. because the sintering which occurs at the higher temperature is said to destroy the catalytic activity. Accepted prior art belief has generally been to the effect that calcination above 1000° F. may sinter catalyst metals and destroy active catalyst sites.

The catalyst support, in $NH_4^+$ or more preferably in $H^+$ form, so obtained is loaded with a metal of the platinum-palladium group: platinum, iridium, osmium, palladium, rhodium, or ruthenium. Preferred metals include platinum and palladium and more preferably palladium. A loading of 0.1 w %–10 w %, say 2 w % palladium may be employed.

Catalyst containing metal-on-hydrogen mordenite is obtained by immersing the catalyst support in preferably aqueous solutions containing soluble salts (such as palladium nitrate) of the metals—preferably in several steps after each of which the loaded catalyst composition may be dried at 212° F.–1000° F., preferably raising the temperature in steps over an eight hour period to 1000° F.

The metal is distributed substantially as 50–500 A crystals over the surface of the mordenite crystals.

When the final catalyst composition is formulated, it may be dried at 212° F.–1000° F., preferably raising the temperature in steps over an eight hour period to 1000° F. before calcining.

It is a feature of the process of this invention that the final loaded catalyst composition must have been calcined at 1200° F.–1500° F., preferably 1250° F.–1350° F., say 1300° F. for 2–24, say 15 hours prior to use in isomerization.

It is for example possible to carry out this high temperature calcination in the following manner:

(i) calcine the catalyst support, prior to loading with metal, at 1200° F.–1500° F., say 1300° F. for 15 hours followed by calcination of the loaded support at temperature of 1200° F.–1500° F. for 2–24 hours, say 15 hours, or more preferably:

(ii) calcine the catalyst support prior to loading with metal, at a temperature below 1200° F.–1500° F., say typically 1000° F.–1200° F., say 1000° F. for 1–15 hours, say 8 hours followed by calcination of the loaded support at 1200° F.–1500° F., say 1300° F. for typically 2–24 hours, say 15 hours.

Regardless of which of these techniques is used to prepare the final catalyst composition, the mordenite, will have been modified or activated. It is found that heating the catalyst to 1200° F.–1500° F., after it has been loaded with metals from aqueous solution, converts the Bronsted sites (formed during contact with aqueous media) to desired active sites.

Specifically it appears that the Bronsted acid sites (formed during deposition of metals from aqueous media) which are substantially untouched at temperatures below about 1200° F. are converted, at temperatures above about 1200° F., to Lewis acid sites which are activated sites for various reactions including isomerization, trans-alkylation, disproportionation, etc. Calcining the catalyst composition at 1200° F.–1500° F. after the composition has been exposed to water for the last time, permits attainment of composition characterized by presence of active isomerization sites. Specifically its found that the number of desired Bronsted sites in the mordenite which has been calcined to 1200° F.–1500° F. is less than about 50% of the number found in mordenite which has been calcined at say 1000° F. In fact calcining at the upper portion of the 1200° F.–1500° F. range reduces the Bronsted sites to a minimum. It is found that the desired Lewis acid sites so formed are retained if the catalyst composition be maintained (and used) under substantially anhydrous conditions, as water will regenerate the Bronsted sites.

It is also unexpectedly found that calcining the mordenite catalysts of this invention under the noted conditions desirably decreases the cracking activity of the catalyst composition when isomerization is carried out at 400° F.–500° F.

It is a feature of this invention that this increased isomerization activity is found in acid mordenites having a silica to alumina ratio which is above about 10:1. As the ratio increases to about 20:1, the maximum isomerization activity is observed (for 1300° F. calcination of loaded mordenite) and as the ratio increases to about 60:1, the degree of isomerization drops to a level at which it is no longer desirable. It appears that it is desirable to operate in the range of 10–50:1, more preferably 10–30:1; and generally a ratio of 20:1 may be preferred.

It may be noted however that the preferred ratio may vary depending on the desiderata. By way of illustration, it is possible by using a catalyst having a ratio of 10:1, calcined at 1300° F. after deposition of metal, to obtain an isomate yield of 18% with no cracked product. Use of a 20:1 mordenite, calcined at 1300° F., may double the isomate yield to 36%, but undesirably increases the yield of cracked product to 13%. Generally it is observed that use of lower ratios, preferably 10:1, gives higher ratio of isomate to cracked product; while higher ratios up to 20:1 give more isomate but at lower ratio of isomate to cracked product. Use of silica to alumina ratios as high as 60:1 generally gives lower yield of isomate and cracked product and lower ratio of isomate to cracked product.

Expressed differently, the selectivity and conversion to desired isomate is highest in the range of ratios of 10–20:1.

A preferred catalyst to be employed in practice of the process of this invention may be a 2 w % palladium-on-hydrogen mordenite (20:1 weight ratio of silica-to-alumina) which has been calcined at 1300° F. after being loaded with palladium.

The hydrocarbons which may be isomerized by the process of this invention may include paraffinic or olefinic hydrocarbons typically having 4–20, preferably 4–12, say 8 carbon atoms; aromatic hydrocarbons typified by xylenes; olefins typically having 4–20, preferably 4–12, say 8 carbon atoms; etc. The preferred charge stock may include paraffinic hydrocarbons typified by n-butane, n-hexane, n-heptane, n-octane, n-decane, n-dodecane, etc.

The instant catalyst may find use in isomerization processes wherein the position of the double bond is changed as typified by the conversion of butene-1 to butene-2. It may also find use in disproportionation processes such as the conversion of toluene to benzene and xylene or in transalkylation processes such as the reaction of benzene and xylene to prepare toluene.

Prior to use of the calcined catalyst composition, it is preferred to precondition the composition by heating, in a flowing stream of hydrogen, to 450° F.–1000° F., preferably 500° F.–675° F. say 550° F. for 3–24 hours, preferably 10–20 hours, say 15 hours—followed by maintaining at 700° F.–800° F., say 780° F. for 1–2 hours, say 2 hours. Pretreating, like isomerization, is preferably carried out under substantially anhydrous conditions.

Isomerization in accordance with the process of this invention may be carried out by passing the charge isomerizable hydrocarbon into contact with the preconditioned catalyst in the presence of hydrogen, at the following conditions:

TABLE

| Condition | Broad | Preferred | Typical |
|---|---|---|---|
| Temperature °F. | 400–500 | 400–450 | 435 |
| Pressure psig | 0–100 | 0–50 | 0 |
| LHSV | 0.1–20 | 0.1–2 | 1 |
| Hydrogen rate SCFB | 1000–5000 | 1500–2500 | 2300 |

The catalyst may be in the form of granules, e.g. 10 to 25 mesh Tyler Standard Screen Scale, and preferably is in the form of pellets or extrusions having a diameter of about 1/16 inch. The reaction is suitably carried out over a fixed bed of catalyst with the hydrogen and feedstock passing downwardly through the catalyst bed. Unreacted hydrogen may be separated from the effluent stream from the catalyst bed and recycled to the process.

Operating temperature and catalyst activity are correlated with space velocity to give reasonably rapid processing of the feedstock at catalyst deactivation rates which insure maximum on-stream time of the catalyst between periods of regeneration.

As the catalyst ages, its activity for the desired reaction tends to slowly diminish. The catalyst may be maintained at or periodically brought back to approximately its initial level of activity by increasing the operating temperature as the catalyst ages.

The stream leaving the isomerization operation may be characterized by high conversion and by high selectivity to desired products. In the isomerization of normal paraffins, for example, operation under preferred conditions leads to conversions of 40%–62%, say 50%. Selectivity to desired isomate may be 40%–100%, say 75%. Susceptibility to cracking increases with hydrocarbon chain length. Selectivity of better than 95% is attained during isomerization of normal heptane. In the case of normal dodecane, selectivity may be as low as 73%. The ratio of yield of undesirable cracked product to isomate yield may be 0–3:1.

It may be possible to effect disproportionation of disproportionable hydrocarbons by the process of this invention. Typical of such hydrocarbons are aromatic hydrocarbons such as toluene (which produce benzene and xylenes); olefines such as butene-1 (which produce butadiene and butanes); etc.

Disproportionation conditions may include:

TABLE

| Condition | Broad | Preferred | Typical |
|---|---|---|---|
| Temperature °F. | 600–1100 | 600–900 | 750 |

TABLE-continued

| Condition | Broad | Preferred | Typical |
|---|---|---|---|
| Pressure psig | 0–1500 | 0–500 | 250 |
| LHSV | 0.1–20 | 0.5–2 | 1 |

It may also be possible to effect transalkylation of transalkylatable hydrocarbons by the process of this invention. Typical of such reactions may be (i) the reaction of benzene and xylenes to prepare toluene, (ii) the reaction of toluene and higher alkylbenzenes to prepare xylenes; etc.

Transalkylation conditions may include:

TABLE

| Condition | Broad | Preferred | Typical |
|---|---|---|---|
| Temperature °F. | 750–850 | 750–800 | 750 |
| Pressure psig | 0–3000 | 0–500 | 250 |
| LHSV | 0.2–1.0 | 0.5–1 | 1.0 |

DESCRIPTION OF PREFERRED EMBODIMENTS

Practice of the process of this invention may be apparent to those skilled in the art from inspection of the following wherein, as elsewhere in this application, all parts are parts by weight unless otherwise stated.

EXAMPLE I

In the series of runs which make up this Example, three different hydrogen mordenites are employed:viz, those having a weight ratio of silica-to-alumina of 10:1, of 20:1, and of 60:1. Each mordenite sample is loaded with 2 w % palladium from an aqueous solution of palladium chloride and then dried at 212° F. for 15 hours. The loaded mordenite is then calcined at the temperature indicated in the following table for 15–19 hours. It is then preconditioned in hydrogen at a rate of 50 cc per hour per cc of catalyst at 300° F./1 atm for 15–19 hours followed by a period of 2 hours at 780° F.

Isomerization of charge n-dodecane is effected at 400° F./1 atmosphere pressure and 1 LHSV. Hydrogen flow rate is 50 volumes per minute volume of catalyst. Runs are carried out for five hours and the following table sets forth the results in terms of yield of isomate and yield of cracked product. By way of illustration, the entry 36/13 in the Table indicates that when the catalyst composition is 2 w % palladium-on-hydrogen mordenite (the loaded catalyst having been calcined at 1300° F.), the product of reaction contains 36 w % of isomate and 13 w % of cracked products.

TABLE

| Calcination Temp. °F. | $SiO_2:Al_2O_3$ Ratio of Mordenite | | |
|---|---|---|---|
| | 10:1 | 20:1 | 60:1 |
| 1480 | | | 1/0 |
| 1400 | 7/1 | 17/4 | |
| 1300 | 18/0 | 36/13 | 2/9 |
| 1200 | 12/16 | 9/26 | 1/3 |
| 1000 | 0/6 | 0/100 | 3/7 |
| Uncalcined | 0/100 | 5/24 | 14/10 |

Results in terms of isomate w % yield/crackate w % yield

From this Table, it will be apparent to those skilled in the art that best yields of isomerized product are attained when using mordenite having a silica-to-alumina ratio of 10–20:1 which has been calcined at a calcination temperature of 1200° F.–1500° F.; the product contains as much as 36 w % of isomerized dodecanes. It will be noted that use of a 2 w % palladium-on-mordenite (silica-to-alumina ratio of 10:1) which has been activated at 1300° F. gives product containing a substantial portion (18 w %) of isomerized product and which is substantially free of cracked product.

Generally isomate yield is poor and cracking bothersome when the catalyst is either uncalcined or is calcined at 1000° F. Isomate yield improves (as does Selectivity) with increasing calcination temperature up to about 1300° F. A "center of gravity" calculation indicates that about 1313° F. is optimum for activating the 20:1 ratio mordenite, while 1286° F. appears to be optimum for the 10:1 mordenite. It should be noted that the 60:1 ratio mordenite could not be thermally activated for isomerization as evidenced by low yield of dodecane isomate.

EXAMPLES II–IV

In these Examples, 2 w % palladium-on-mordenite catalysts are prepared on mordenites of various silica-to-alumina ratios. The palladium-on-mordenite catalyst is either (i) uncalcined i.e. merely dried at 212° F. for 15 hours prior to hydrogen preconditioning, in control Examples III*–VI* or (ii) calcined at 1300° F., in experimental Example II.

Charge composition and reaction conditions are identical to those of Example I except that isomerization of Example V is carried out at 410° F.

The following Table lists (i) the isomate obtained as weight % of the charge n-dodecane, (ii) the cracked product obtained, both liquid and gas, on the same basis and (iii) the Deactivation Time (hours). The latter is determined by the intercept with the log t axis of a plot of conversion to isomate as a function of log t (i.e. wherein time is in hours).

TABLE

| Example | Ratio | Isomate | Crackate Gas | Crackate Liquid | Deactivation Time hrs |
|---|---|---|---|---|---|
| II | 20 | 36 | 9 | 4 | 163 |
| III* | 20 | 5 | 21 | 3 | 13 |
| IV* | 10 | 0 | 100 | 0 | 0 |
| V* | 10 | 9 | 10 | 4 | 14 |
| VI* | 60 | 14 | 7 | 3 | 13 |

*Control
Deactivation time is the time (hours) required to lose isomerization activity.

From inspection of the Table, it is apparent that the experimental catalyst of Example II (calcined at 1300° F.) has a deactivation time (163 hours) which is 12+ times that of the best (13–14 hours) of the control Examples. It is also apparent that the run of Example II produced almost three times as much isomate as did the runs of the best of the other Examples. Other conclusions will be apparent to those skilled in the art.

EXAMPLES VII–VIII*

In this pair of comparative examples, experimental Example VIII, a preferred embodiment of the process of this invention, utilizes a 2 w % palladium-on-mordenite (silica-to-alumina ratio of 20:1) which was prepared as in Example I. Calcination temperature is 1300° F. after palladium loading. Preconditioning and reaction are as in Example I. Charge hydrocarbon is n-heptane.

As control Example VIII*, the results set forth in Table 10 of British No. 1,088,933 are set forth. The results of the British patent, expressed in mole %, are converted to weight %.

The Table below sets forth the content of the product from isomerization and the Conversion and Selectivity.

TABLE

| Hydrocarbon Product | Example VII | Example VIII* |
|---|---|---|
| Unconverted heptane | 37.6 | 45 |
| Dimethyl pentane | 10.2 | 1.1 |
| 2-methyl hexane | 26.1 | 9.9 |
| 3-methyl hexane | 22.4 | 11.- |
| 3-ethyl pentane | 2.4 | 0 |
| Cracked Product | 1.3 | 33 |
| Conversion w % | 62.4 | 55 |
| Selectivity w % | 98 | 40 |

From the above Table, it will be observed that the Conversion and Selectivity of the experimental Example VII are substantially superior to those of control Example VIII*. The amount of cracked product of the experimental (1.3%) is substantially smaller than that of the control example (33%). Other conclusions will be apparent to those skilled in the art.

EXAMPLE IX

In this example, transalkylation may be effected by use of the same preferred catalyst as used in Example VII. Charge contains benzene and xylenes in mole ratio of 1.1 moles of xylene per mole of benzene, LHSV is 1.0. Reaction is carried out at 750° F. and 250 psig in the presence of hydrogen in amount of 2300 SCFB. Product transalkylate is found to contain toluene.

EXAMPLE X

In this example, disproportionation may be effected by use of the same preferred catalyst as used in Example VII. Charge is toluene at LHSV of 1.0. Reaction is carried out at 750° F. and 250 psig in the presence of hydrogen in amount of 2300 SCFB. Product disproportionate is found to contain benzene and xylenes.

Although this invention has been illustrated by reference to specific embodiments, it will be apparent to those skilled in the art that various changes and modifications may be made which clearly fall within the scope of this invention.

I claim:

1. The method of isomerizing an isomerizable hydrocarbon charge which comprises
    passing an isomerizable hydrocarbon charge at isomerization conditions into contact with as isomerization catalyst, a hydrogen mordenite catalyst, having a silica-to-alumina mole ratio of 10–20:1, loaded with a metal of the platinim-palladium group, said catalyst containing activated isomerization sites formed by calcining at 1200° F.–1500° F. after loading, thereby forming product isomate; and recovering said product isomate.

2. The method of isomerizing as claimed in claim 1 wherein said charge contains n-paraffin.

3. The method of isomerizing as claimed in claim 3 wherein said metal is palladium.

4. The method of isomerizing as claimed in claim 1 wherein said isomerization conditions include temperature of 400° F.–500° F.

5. The method of isomerizing an isomerizable hydrocarbon charge containing normal paraffins which comprises
    passing an isomerizable hydrocarbon charge at isomerization conditions including temperature of 400°

F.–500° F. into contact with, as isomerization catalyst, a hydrogen mordenite catalyst, having a silica-to-alumina mole ratio of 10–20:1, loaded with 0.5 w %–2.5 w % palladium, said catalyst containing activated isomerization sites formed by calcining at 1200° F.–1500° F. after loading thereby forming a product isomate; and recovering said product isomate.

* * * * *

UNITED STATES PATENT AND TRADEMARK OFFICE
CERTIFICATE OF CORRECTION

PATENT NO. : 4,489,216

DATED : 18 December 1984

INVENTOR(S) : Paul H. Lewis

It is certified that error appears in the above-identified patent and that said Letters Patent is hereby corrected as shown below:

On the title page;

Correct the spelling of the attorney's name to read --Carl G. Seutter--

Col. 1, line 38 "50.1" should read -- 50:1 --;

line 65, cancel the "comma," insert a -- semi-colon --

Column 2, line 4, correct the formula to read as follows:

$$M_{8/n} \cdot Al_8 Si_{40} \cdot O_{96} \cdot 24H_2O$$

Signed and Sealed this

Tenth Day of September 1985

[SEAL]

Attest:

DONALD J. QUIGG

Attesting Officer     Acting Commissioner of Patents and Trademarks - Designate